(12) United States Patent
Butler et al.

(10) Patent No.: US 8,172,879 B2
(45) Date of Patent: May 8, 2012

(54) RESILIENT SPINAL ROD SYSTEM WITH CONTROLLABLE ANGULATION

(75) Inventors: Michael S. Butler, St. Charles, IL (US); Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 527 days.

(21) Appl. No.: 12/196,438

(22) Filed: Aug. 22, 2008

(65) Prior Publication Data

US 2009/0054932 A1 Feb. 26, 2009

Related U.S. Application Data

(60) Provisional application No. 60/965,971, filed on Aug. 23, 2007.

(51) Int. Cl.
*A61B 17/70* (2006.01)
(52) U.S. Cl. .......................... 606/255; 606/259
(58) Field of Classification Search .......... 606/250–263; 403/223
See application file for complete search history.

(56) References Cited

U.S. PATENT DOCUMENTS

| | | | |
|---|---|---|---|
| 4,041,939 A * | 8/1977 | Hall | 606/254 |
| 4,804,000 A | 2/1989 | Lamb et al. | |
| 5,034,011 A | 7/1991 | Howland | |
| 5,047,029 A | 9/1991 | Aebi et al. | |
| 5,466,238 A | 11/1995 | Lin | |
| 6,241,730 B1 | 6/2001 | Alby | |
| 6,290,700 B1 | 9/2001 | Schmotzer | |
| 6,736,818 B2 | 5/2004 | Perren et al. | |
| 7,326,210 B2 | 2/2008 | Jahng et al. | |
| 7,556,639 B2 | 7/2009 | Rothman et al. | |
| 7,621,940 B2 | 11/2009 | Harms et al. | |
| 7,815,665 B2 * | 10/2010 | Jahng et al. | 606/263 |
| 2004/0039384 A1 | 2/2004 | Boehm et al. | |
| 2005/0038432 A1 | 2/2005 | Shaolian et al. | |

(Continued)

FOREIGN PATENT DOCUMENTS

FR 2715825 8/1995

(Continued)

OTHER PUBLICATIONS

Written Opinion of the International Searching Authority for PCT Application No. PCT/US08/74019, mail date Nov. 3, 2008, 4 pages.

*Primary Examiner* — Eduardo C Robert
*Assistant Examiner* — Mary Hoffman
(74) *Attorney, Agent, or Firm* — Foley & Lardner LLP

(57) ABSTRACT

A spinal rod includes a rod tube formed of a biocompatible material, a spring rod formed of a biocompatible material and having a spring rod portion disposed in the rod tube, the spring rod portion axially movable within the rod tube whereby application of an axial force on the spring rod portion creates axial movement of the spring rod relative to the rod tube causing the spring rod and the rod tube to flex and arch, and a spacer ring radially disposed between the rod tube and the spring rod.

25 Claims, 4 Drawing Sheets

U.S. PATENT DOCUMENTS

| | | |
|---|---|---|
| 2005/0065514 A1 | 3/2005 | Studer |
| 2005/0085815 A1 | 4/2005 | Harms et al. |
| 2005/0113927 A1 | 5/2005 | Malek |
| 2005/0124991 A1 | 6/2005 | Jahng |
| 2005/0131407 A1 | 6/2005 | Sicvol et al. |
| 2005/0143823 A1 | 6/2005 | Boyd et al. |
| 2005/0165396 A1 | 7/2005 | Fortin et al. |
| 2005/0182409 A1 | 8/2005 | Callahan et al. |
| 2005/0222569 A1 | 10/2005 | Panjabi |
| 2006/0106381 A1 | 5/2006 | Ferree et al. |
| 2006/0229612 A1 | 10/2006 | Rothman et al. |
| 2006/0264935 A1 | 11/2006 | White |
| 2006/0264937 A1 | 11/2006 | White |
| 2007/0118122 A1 | 5/2007 | Butler et al. |

FOREIGN PATENT DOCUMENTS

| | | |
|---|---|---|
| WO | WO-2009/026519 A1 | 2/2009 |

* cited by examiner

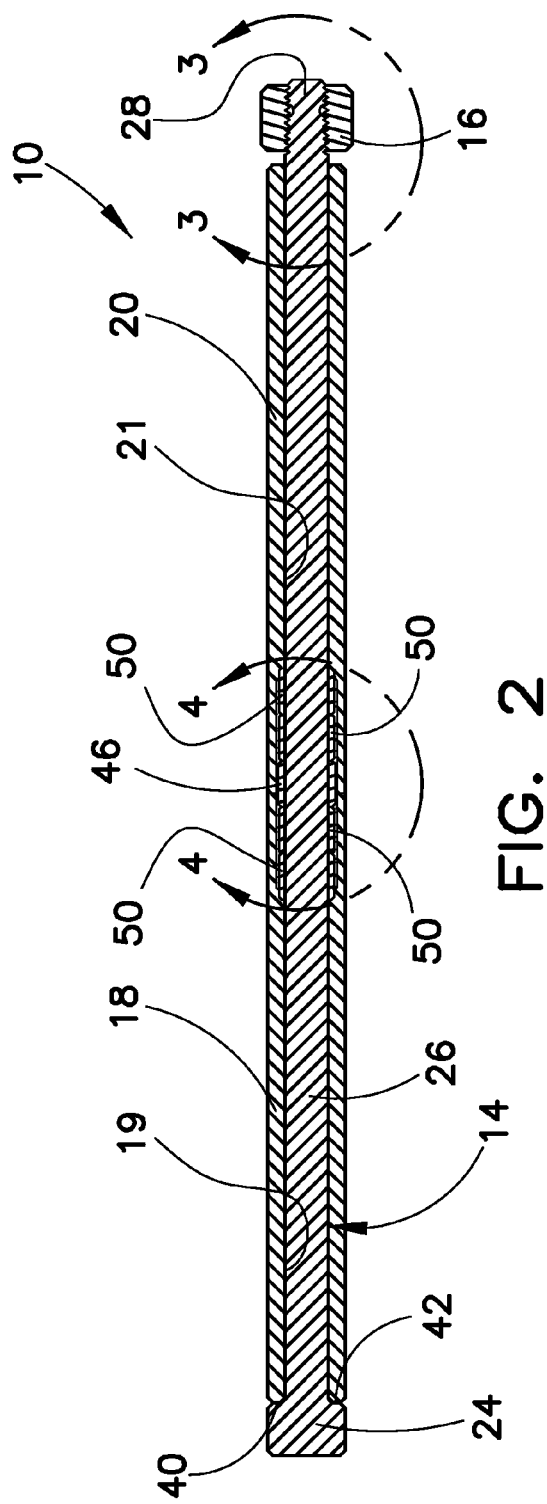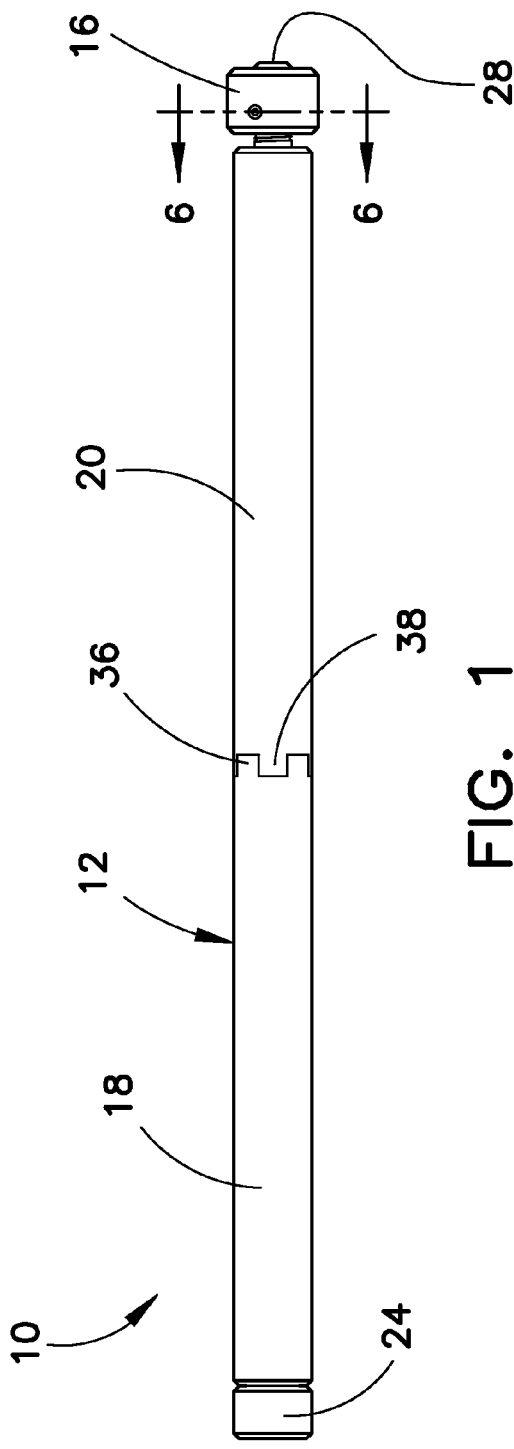

RESILIENT SPINAL ROD SYSTEM WITH CONTROLLABLE ANGULATION

RELATED APPLICATIONS

This patent application claims the benefit of and/or priority to U.S. Provisional Patent Application Ser. No. 60/965,971 filed Aug. 23, 2007, entitled "Resilient Spinal Rod System With Controllable Angulation" the entire contents of which is specifically incorporated herein by this reference.

BACKGROUND

1. Field of the Invention

The present invention relates to devices for the stabilization of the spinal column such as and particularly spinal rods for the stabilization of vertebrae of the spine and, more particularly, to a resilient spinal rod system for the stabilization of vertebrae of the spine.

2. Background Information

A significant portion of the population suffers from spinal problems. Such spinal problems may be attributable to disease, trauma and/or other event. In the case of degenerative disc disease, spinal trauma and the like, such conditions are often painful and/or physically deforming. Depending on the situation the pain and complications caused by these conditions may require that one or more vertebra, facet joints, and/or intervertebral discs be removed from the spinal column. In these procedures, bone fusion is a common treatment used to facilitate the realignment and/or fixation of the remaining spinal elements.

Currently, two types of systems or assemblies are utilized for securing and/or stabilizing one or more vertebrae in order to achieve bone fusion. One type of spine stabilizing assembly generally includes two posterior vertebral plates disposed longitudinally on either side of the spinous processes. Each plate is attached between adjacent vertebra using bone anchoring elements, such as bone screws. Together, the plates provide a rigid vertebral fixation.

Another type of spine stabilizing assembly generally includes two posterior vertebral rods disposed longitudinally on either side of the vertebrae (e.g. the spinous processes thereof). Like the plates, these rods are attached between adjacent vertebrae using appropriate bone anchoring devices to achieve rigid vertebral fixation.

These spine stabilizing assemblies are also used to correct spinal deformities such as scoliosis or the like. For this use, such spine stabilizing assemblies may have spine rods that span two or more vertebrae.

A drawback of rigid fixation relates to the loading that occurs on the stabilizing assemblies and especially on the anchoring sites during normal activity. These loads may result in loosening of the assembly from the vertebrae or even breaking of the assembly. Also, fusion subjects the non-fused spine elements to various stresses, particularly the remaining adjacent vertebrae and vertebral discs since these elements must accommodate different degrees of motion. Moreover, spinal fusion limits the range of a patient's motion.

Because of the drawbacks to rigid spine fixation systems, semi-rigid spine fixation systems have been proposed that aim to allow limited intervertebral movement for promoting bone fusion and/or reducing spine stress. These semi-rigid spine fixation systems, however, are far from effective and/or efficient.

There is thus a need for a spine stabilization device, assembly and/or system that allows for bending.

There is also a need for a spine stabilization device, assembly and/or system that allows for in-situ bending pre-bending and/or both.

There is also a need for a spine stabilization device, assembly and/or system that allows for controllable bending.

These needs and others are accomplished through application of the principles of the subject invention.

SUMMARY OF THE INVENTION

The present invention provides a resilient spinal rod/rod system with controllable angulation or curvature. The present spinal rod is particularly, but not necessarily, for posterior spine stabilization. The controllable curvature of the present resilient spinal rod allows for limited movement of the vertebrae connected by the present resilient spinal rod system.

The present resilient spinal rod system is thus bendable along its longitudinal axis and configured to maintain its curvature or angulation. Such angulation may be set during manufacture or may be set in-situ.

The present resilient spinal rod with controllable angulation is defined by a multi-component system which includes an inner spring rod and an outer rod tube. An angulation ring is threadedly attached to an end of the spring rod and provides controlled adjustment of the angulation of the spinal rod through axial compression of the spring rod relative to the outer tube. The angulation ring and thus the angulation of the spinal rod are fixed via an angulation pin that locks the angulation ring relative to the spring rod. This prevents the increase and/or decrease of angulation of the spinal rod once locked.

The present resilient spinal rod with controllable angulation may include a titanium spacer ring that is situated between the spring rod and the outer rod tube in order to prevent and/or hinder over angulation. The spacer ring may be situated midpoint of the length of the spinal rod.

Additionally, one or more spacer rings are situated between the spring rod and the outer rod tube axially adjacent each side of the titanium spacer ring. The spacers may be made of polycarbonate urethane. The spacer rings act as an additional spring force in bending, and act as a shock absorber in the axial compression of the of the spinal rod. Preferably, the outer periphery of a spacer ring has a slight inward taper from each end toward its axial midpoint to control collapse of the spacer ring. The rings may be made of various durometers.

In one form, the spring rod is made from hardened titanium (Ti 6AL4VELI) so as to give the spring rod a spring temper.

In one form, the outer rod tube is formed of two portions that connect to each other preferably at a midpoint of the spring rod. An end of each outer rod tube portion is formed in a stepped or "castle" shape that interlock with each other to prevent and/or hinder rotation of the outer rod tube portions.

The present spinal rod may be straight or curved (lordosed) and may be made in different lengths. The spinal rod may be made to have various curvatures. A stabilization system may include straight and curved spinal rod segments.

BRIEF DESCRIPTION OF THE DRAWINGS

The features and objects of this invention, and the manner of attaining them, will become more apparent and the invention itself will be better understood by reference to the following description of an embodiment of the present invention taken in conjunction with the accompanying drawings, wherein:

FIG. 1 is a side view of a resilient spinal rod with controllable angulation fashioned in accordance with the present principles;

FIG. 2 is a sectional view of the resilient spinal rod with controllable angulation of FIG. 1 taken along line 2-2 thereof;

Figure 3:
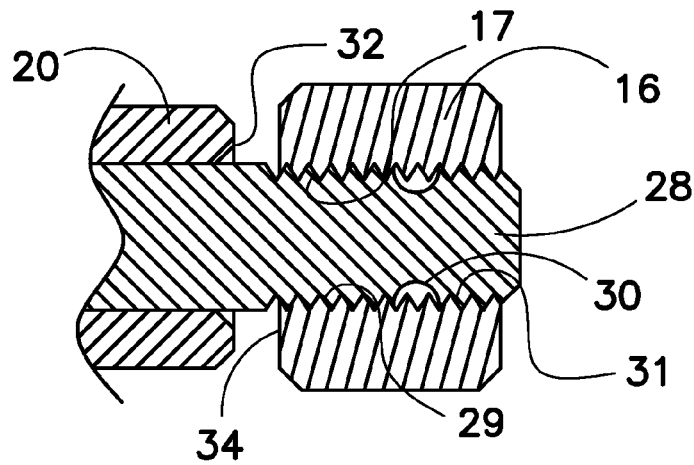
FIG. 3 is an enlarged view of a portion of the sectional view of the resilient spinal rod with controllable angulation of FIG. 2 taken along circle 3-3 thereof.

An overview of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF A PREFERRED EMBODIMENT

Referring to the figures, there is depicted an embodiment of a resilient spinal rod/rod system with controllable angulation (bending or curving) 10 (generally, spinal rod 10), fashioned in accordance with the present principles and especially for use in a spinal stabilization system or assembly. The spinal rod 10 is designed to be retained at both ends to respective bone anchoring elements (not shown) such as are known in the art. The spinal rod 10 is fashioned from a biocompatible material such as titanium, stainless steel or the like.

The spinal rod 10 is characterized by a rod tube or cylinder 12 that surrounds a portion of a spring rod 14. The rod tube 12 is preferably, but not necessarily, formed by first and second rod tube portions 18 and 20. The first and second rod tube portions 18 and 20 each have a first end that is stepped or castled, i.e. ends 36 and 38 of respective first and second rod tube portions 18 and 20, that are joined together at an approximate mid point or middle of the axial length of the spring rod 14. The stepped first ends 36 and 38 prevent and/or hinder rotation of the rod tube portions 18 and 20 relative to the spring rod 14.

Figure 7:
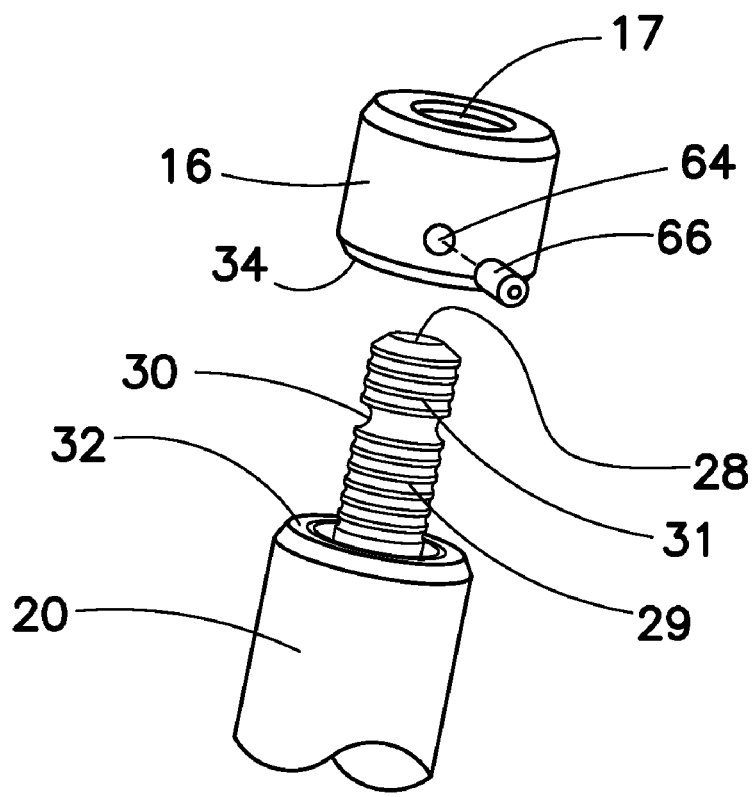
FIG. 7 is a partial view of an end of the resilient spinal rod with controllable angulation of FIG. 1 showing an end cap thereof in exploded view.

The spring rod 14 has a rod portion 26 that axially extends a length from a cylindrical head 24. The rod portion 26 extends through and within an axial bore 19 of the first rod tube portion 18 and an axial bore 21 of the second rod tube portion 20. A second end 40 of the first tube portion 18 abuts the cylindrical head 24. The rod portion 26 of the spring rod 14 terminates in an end 28 distal the cylindrical head 24. As best seen in FIGS. 3 and 7, the end 28 has first external threading 29 and second external threading 31 separated by an annular groove 30. The threaded end 28 accepts an angulation ring 16. The angulation ring 16 includes an internally threaded bore 17. The angulation ring 16 is thus threadedly received onto the threaded end 28. As discussed further below, the angulation ring 16 adjusts the curvature, bend or angulation of the spinal rod 10.

Figure 4:
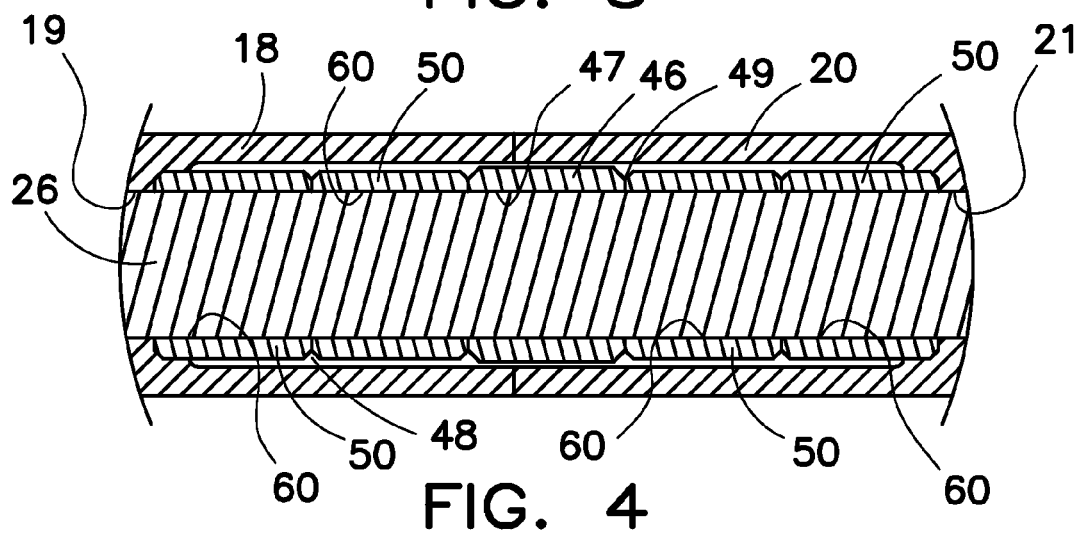
FIG. 4 is an enlarged view of a portion of the sectional view of the resilient spinal rod with controllable angulation of FIG. 2 taken along circle 4-4 thereof.

As best seen in FIG. 4, the spinal rod 10 includes an essentially tubular spacer ring 46 that radially surrounds the rod portion 26. The spacer ring 46 is preferably, but not necessarily, made from titanium and is situated about the rod portion 26 at the middle or mid point of the length of the rod portion 26, and particularly, radially inward of the first ends 36 and 38 of the first and second rod portions 18 and 20. It should be appreciated that the spacer ring 46 may be provided at different places along the rod portion 26 and/or more than one spacer ring 46 may be provided. The spacer ring 46 prevents and/or hinders over angulation of the spinal rod 10.

With continuing reference to FIG. 4, the spinal rod 10 also includes one or more (here, four) essentially tubular spacer rings 50 that radially surround the rod portion 26. These are shown and described as polycarbonate urethane (PCU) spacer rings but may be of a different material and of different durometers It should be appreciated that while the spinal rod 10 has four PCU spacer rings 50, a spinal rod fashioned in accordance with the present principles may have more or less than four PCU spacer rings 50 or no spacer rings. In the case of no spacer rings, titanium spacers or wire cuts or other material washers may be used for the spring effect. Two of the four PCU spacer rings 50 are positioned to one axial side of the spacer ring 46 while the other two of the four PCU spacer rings 50 are positioned to the other axial side of the spacer ring 46. Axial positioning of the PCU spacer rings 50 may be changed as desired. The PCU spacer rings 50 act as an additional spring force in bending and as a shock absorber in axial compression of the spinal rod 10. It should be appreciated that the spacer ring 26 may be used without the PCU spacer rings 50, while the PCU spacer rings 50 may be used without the spacer ring 26.

Figure 5:
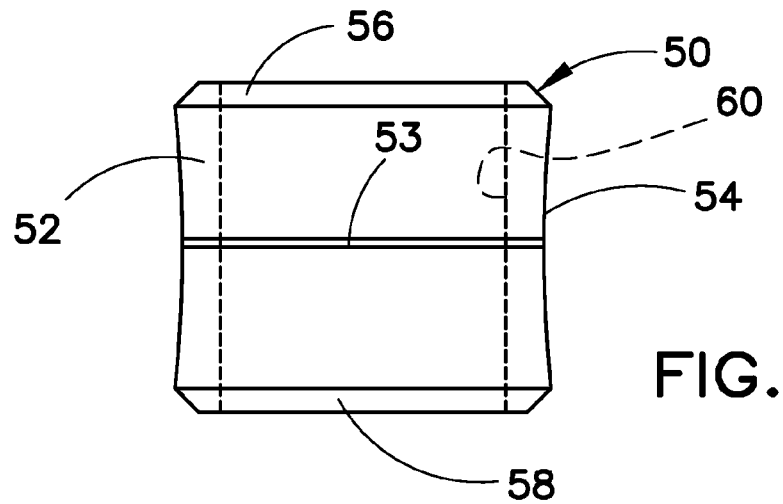
FIG. 5 is an enlarged side view of a spacer ring of the resilient spinal rod with controllable angulation of FIG. 1.

An enlarged PCU spacer ring 50 is shown in FIG. 5 and reference is now made thereto. The spacer ring 50 includes a generally tubular body 52 have a central bore 60 extending from one tapered end 56 to another tapered end 58. The body 52 includes a curved outer periphery or wall 54 that radially inwardly arches from the tapered ends 56 and 58 towards a midpoint 53. The curved outer wall 54 controls collapse of the PCU spacer ring 50 during angulation. The PCU spacer rings 50 may be made of various durometers to provide an additional spring force in bending and as a shock absorber in axial compression of the rod.

In order to accommodate the spacer rings 46 and 50, the first rod portion 18 includes an enlarged bore portion 48 that is greater in diameter than the diameter of the bore 19 of the first rod portion 18. Likewise, the second rod portion 20 includes an enlarged bore portion 49 that is greater in diameter than the diameter of the bore 21 of the second rod portion 20. The axial length of each enlarged bore portion 18, 20 is dependent on the number of spacer rings that the rod portions are to accommodate.

Figure 6:
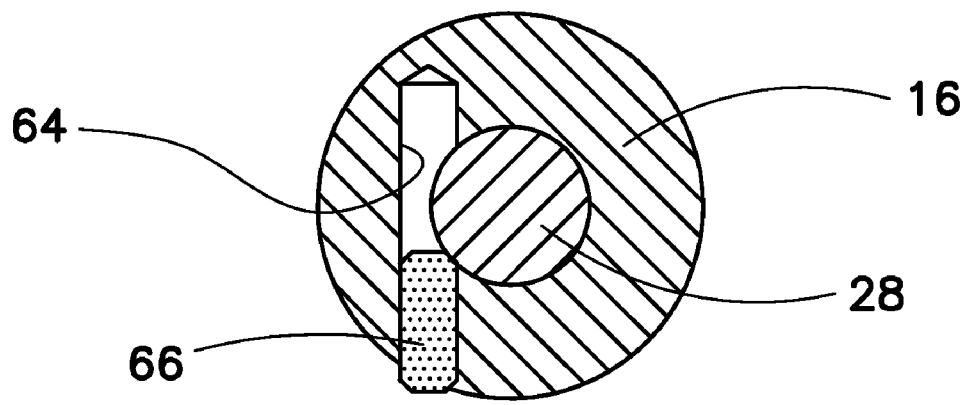
FIG. 6 is an enlarged sectional view of an end portion of the resilient spinal rod with controllable angulation of FIG. 1 taken along line 1-1 thereof.

Referring now to FIGS. 6 and 7, there is shown an enlarged sectional view of the end cap 16 and end structure 28 of the spinal rod 10 and an exploded view of the end cap 16 and end cap pin 66 relative to the end structure 28 respectively, of the spinal rod 10. Once the angulation, bend or curvature of the spinal rod 10 is set by the threading of the end cap 66 onto the end structure 28, the end cap pin 66 is positioned in or pressed into an end cap bore 64 of the end cap 16 such that the end cap pin 66 abuts the threads or pin groove 29 of the end structure 28. The end cap pin 66 thus prevents the end cap 16 from increasing or decreasing the angulation of the spinal rod 10.

Figure 8:
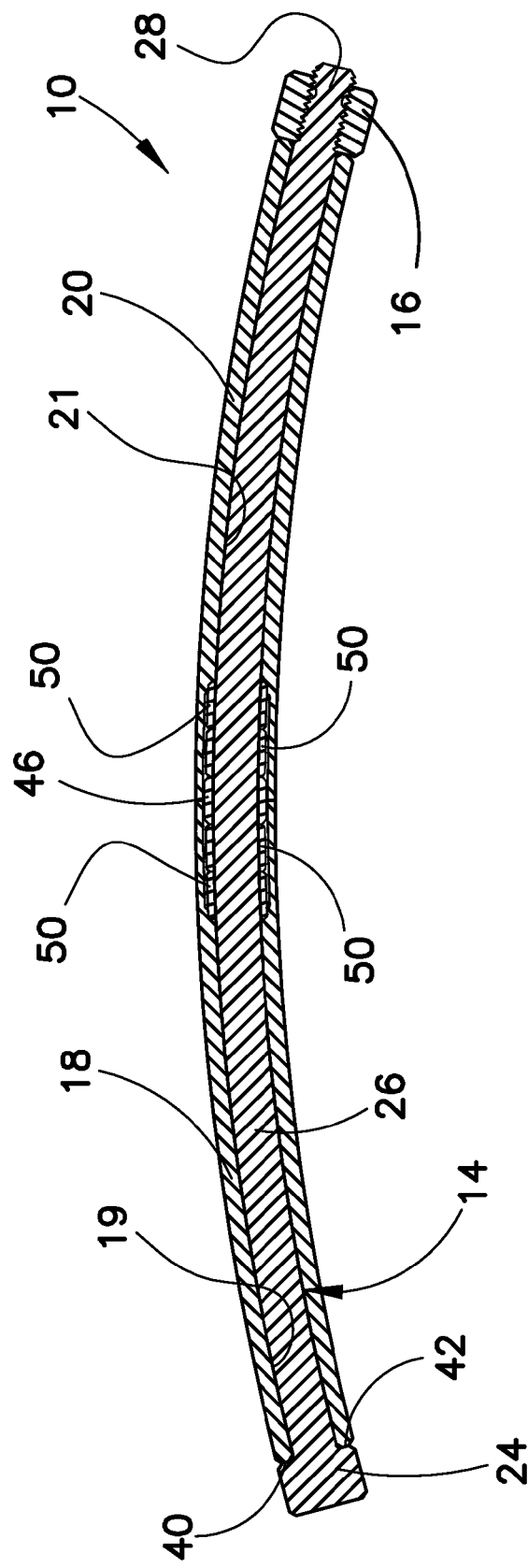
FIG. 8 is a side view of the resilient spinal rod with controllable angulation of FIG. 1 in a lordosed, bent or curved position.

FIG. 8 depicts the spinal rod 10 in an angulated, bent or curved position. The end cap 16 has been threaded onto the end structure 28. As the end 34 of the end cap 16 abuts the end 32 of the second rod portion 20 (see, e.g. FIG. 3), the second rod portion 20 axially compresses or pushes against the first rod portion 18. In turn, the end 40 of the first rod portion 18 axially compresses or pushes against the end 42 of the head 24 of the rod portion 26. Continued compression causes the spinal rod 10 to bend. The spring tension of the rod portion 26 as well as the spring tension of the PCU spacer rings 50 cause the spinal rod 10 to want to spring back to its original, uncompressed position.

The angulation and/or the degree of angulation of the spinal rod 10 may be accomplished and/or set during manufacture of the spinal rod. Alternatively, the angulation and/or degree of angulation of the spinal rod 10 may be accomplished in situ. The spinal rod 10 may be made in different lengths.

It should also be appreciated that the above description is only exemplary of the principles of the subject invention. Therefore, other embodiments are contemplated and within the present scope.

It should moreover be appreciated that the present invention can be further modified within the spirit and scope of this disclosure. This application is therefore intended to cover any variations, uses, of adaptations of the invention using its general principles. Further, this application is intended to cover such departures from the present disclosure as come within known or customary practice in the art to which this invention pertains.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A spinal rod comprising:
   a rod tube formed of a biocompatible material;
   a spring rod formed of a biocompatible material and having a spring rod portion disposed in the rod tube, the spring rod portion axially movable within the rod tube whereby application of an axial force on the spring rod portion creates axial movement of the spring rod relative to the rod tube causing the spring rod and the rod tube to flex and arch; and
   a spacer ring radially disposed between the rod tube and the spring rod;
   at least two secondary spacer rings situated between the spring rod portion and the rod tube and axially adjacent each side of the spacer ring, wherein each one of the secondary spacer rings comprises a curved outer surface having a concave curvature extending inward toward a midpoint of the secondary spacer ring.

2. The spinal rod of claim 1, wherein axial movement of the spring rod relative to the rod tube is controllable whereby arching of the spinal rod is controllable.

3. The spinal rod of claim 2, wherein:
   the spring rod further has a spring rod end element on a first end of the spring rod portion that abuts a first rod tube end, and a threaded section on a second end of the spring rod portion, the threaded section extending a distance axially outwardly from a second rod tube end; and
   further comprising a threaded collar received on the threaded section of the spring rod portion, the threaded collar providing controlled axial movement of the spring rod relative to the rod tube whereby the spring rod end element compresses against the first rod tube end to provide flexing and thus arching of the spinal rod.

4. The spinal rod of claim 3, wherein the threaded collar includes a set pin to rotationally lock the threaded collar to the threaded section thereby fixing the arch of the spinal rod.

5. The spinal rod of claim 1, wherein the spacer ring is configured to hinder over-flexing of the spinal rod.

6. The spinal rod of claim 5, wherein the spacer ring is positioned midpoint of the length of the spinal rod portion.

7. The spinal rod of claim 5, wherein the spacer ring is positioned at either or both ends of the spinal rod portion.

8. The spinal rod of claim 1, wherein the rod tube has a cylindrical groove on an inside surface thereof forming an enlarged bore portion having a relatively larger inner diameter and within which the spacer ring and the secondary spacer rings are situated.

9. The spinal rod of claim 8, wherein the cylindrical groove is disposed at one of a midpoint, end or both ends of the rod tube.

10. The spinal rod of claim 1, wherein the secondary spacer rings are formed of polycarbonate urethane.

11. The spinal rod of claim 1, wherein the secondary spacer rings are made in various durometers.

12. The spinal rod of claim 1, wherein the rod tube is formed of first and second rod tube portions.

13. The spinal rod of claim 12, wherein the first and second rod tube portions are connected to one another at a midpoint of the rod tube.

14. The spinal rod of claim 12, wherein the first and second rod tube portions each include an interlocking configuration on a connection end thereof that hinders rotation of the first and second rod tube portions relative to one another.

15. A spinal rod system having controllable angulation, the spinal rod system comprising:
   a rod tube formed of a biocompatible material and defining a first rod tube end and a second rod tube end;
   a spring rod formed of a biocompatible material and defining a rod portion that is disposed within the rod tube, an end element on a first end of the rod portion exterior to the rod tube and abutting the first rod tube end, and a threaded shank on a second end of the rod portion and extending external to the second end of the rod tube;
   an angulation controller situated on the threaded shank and configured for controlling axial tension on the spring rod through rotation of the angulation controller thereby providing controlled axial movement of the spring rod relative to the rod tube whereby the end element compresses against the first rod tube end to provide angulation of the spinal rod; and
   a spacer ring radially disposed between the rod tube and the spring rod;
   at least two secondary spacer rings situated between the spring rod portion and the rod tube and axially adjacent each side of the spacer ring, wherein each one of the secondary spacer rings comprises an inwardly curved annular surface, the inwardly curved annular surface curving inward from the longitudinal ends of the inwardly curved annular surface to a midpoint of the secondary spacer ring.

16. The spinal rod system of claim 15, wherein the angulation controller comprises a collar having a set pin to rotationally lock the collar to the threaded shank thereby fixing the angulation of the spinal rod.

17. The spinal rod system of claim 15, wherein the spacer ring is configured to hinder over-angulation of the spinal rod.

18. The spinal rod system of claim 17, wherein the spacer ring is situated at one of a midpoint, end or both ends of the length of the spinal rod portion.

19. The spinal rod system of claim 15, wherein the rod tube has a cylindrical groove on an inside surface thereof forming an enlarged bore portion having a relatively larger inner diameter and within which the spacer ring and secondary spacer rings are situated.

20. The spinal rod system of claim 19, wherein the cylindrical groove is disposed at a point where the spacer rings are situated on the rod tube.

21. The spinal rod of claim 15, wherein the secondary spacer rings are formed of polycarbonate urethane.

22. The spinal rod system of claim 15, wherein the secondary spacer rings are made in various durometers.

23. The spinal rod system of claim 15, wherein the rod tube is formed of first and second rod tube portions.

24. The spinal rod system of claim 23, wherein the first and second rod tube portions are connected to one another anywhere along a longitudinal axis of the of the rod tube.

25. The spinal rod system of claim 24, wherein the first and second rod tube portions each include an interlocking configuration on a connection end thereof that limits rotation of the first and second rod tube portions relative to one another.

* * * * *